United States Patent [19]
Dubrul et al.

[11] Patent Number: 4,671,255
[45] Date of Patent: Jun. 9, 1987

[54] TISSUE EXPANDER WITH SELF-CONTAINED INJECTION RESERVOIR AND REINFORCING INSERT

[75] Inventors: William R. Dubrul, Santa Barbara; Charles J. Heyler, III, Thousand Oaks, both of Calif.

[73] Assignee: McGhan Medical Corporation, Santa Barbara, Calif.

[21] Appl. No.: 787,645

[22] Filed: Oct. 16, 1985

[51] Int. Cl.$^4$ .............................................. A61B 19/00
[52] U.S. Cl. ........................................ 128/1 R; 623/7
[58] Field of Search ...................... 623/7, 8; 128/1 R

[56] References Cited

U.S. PATENT DOCUMENTS

| | | | |
|---|---|---|---|
| 3,845,384 | 10/1974 | Stoutenberg et al. | 324/41 |
| 4,190,040 | 2/1980 | Schulte | 128/1 R |
| 4,217,889 | 8/1980 | Radovan et al. | 128/1 R |
| 4,222,374 | 9/1980 | Sampson et al. | 128/1 R |
| 4,428,364 | 1/1984 | Bartolo | 128/1 R |
| 4,574,780 | 3/1986 | Manders | 128/1 R |

OTHER PUBLICATIONS

"Self-Sealing Silicone Valve", by Dow Corning Wright, 2 pages.

Primary Examiner—Dalton L. Truluck
Attorney, Agent, or Firm—Klein & Szekeres

[57] ABSTRACT

A tissue expander, of the type containing within the interior of its expandable shell an injection reservoir self-sealing to punctures by a hypodermic needle, is disclosed. The tissue expander includes a reinforcing member or insert which is substantially more rigid than the expandable shell, is larger than the injection reservoir, and is mounted to the expandable shell with its center substantially at the apex of the shell and substantially superimposed with the center of injection reservoir. The reinforcing member substantially prevents folding of the expandable shell over the injection reservoir and thereby substantially prevents inadvertent puncture of the expandable shell by a needle which is directed into the injection reservoir. Magnetically detectable material is mounted into the injection reservoir to enable an externally applied magnet locator to find the injection reservoir when the entire tissue expander assembly is temporarily implanted in a patient.

23 Claims, 8 Drawing Figures

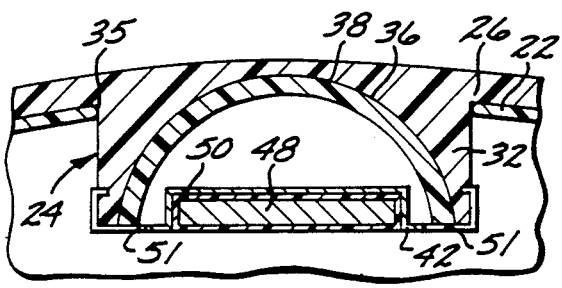
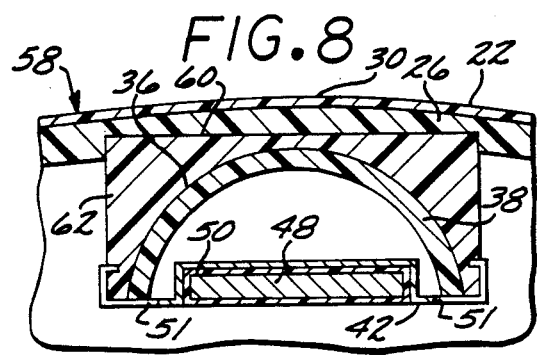
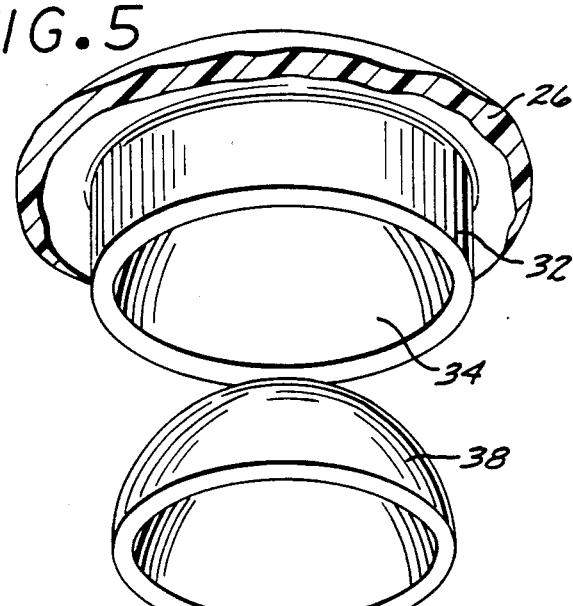
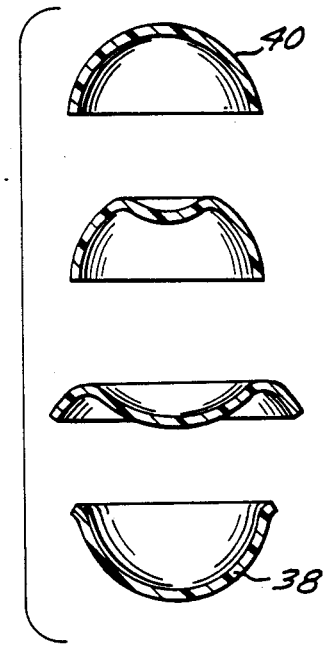
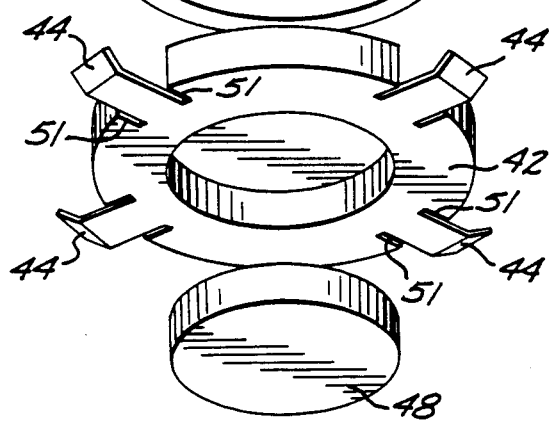
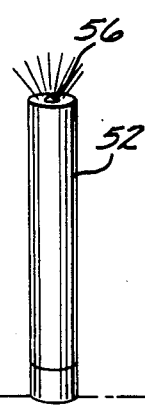
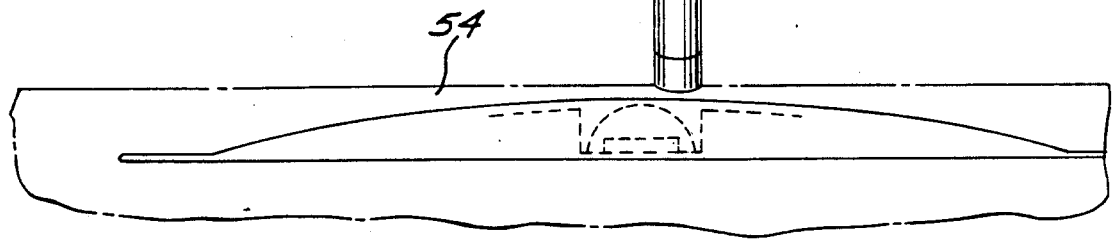

TISSUE EXPANDER WITH SELF-CONTAINED INJECTION RESERVOIR AND REINFORCING INSERT

BACKGROUND OF THE INVENTION

1. Field of the Invention

The present invention is directed to tissue expander devices which are temporarily surgically implanted beneath the skin and subcutaneous layer for the purpose of creating a skin flap or enlargement. More particularly, the present invention is directed to an improved tissue expander device of the type which incorporates an injection reservoir within an inflatable shell of the tissue expander device itself.

2. Brief Description of the Prior Art

The prior art is well aware of tissue expander devices which are temporarily implanted beneath the skin and subcutaneous tissue of humans or domestic animals, and which may be gradually inflated by injection of saline (or similar liquids) for the purpose of causing the growth of a skin flap or enlargement. For a detailed description of such tissue expanders, reference is made to U.S. Pat. No. 4,217,889. Briefly summarized, such tissue expanders comprise a surgically implantable inflatable bag or shell into which the liquid is introduced to gradually enlarge the shell and thereby to cause the desired skin enlargement or flap formation. After the skin flap has formed, the shell is surgically removed. The skin flap is either used, after severance, for purposes of plastic surgery in other parts of the body, or accommodates a permanent implantation directly beneath the flap. Neither the manner of using the skin flap, nor the permanent implants, form part of the present invention.

For medically self-evident reasons, the temporarily implantable inflatable tissue expander shell must not leak, and must not be punctured to form a leak, when, from time to time, additional liquid is introduced into the shell. In some situations, liquid must even be withdrawn from the shell without causing a leak. Such addition or withdrawal of liquid is accomplished, in accordance with standard practice in the art, through a substantially non-expandable bioimplantable injection button or reservoir, which is self-sealing to punctures by a hypodermic needle. Varying constructions of injection buttons or reservoirs are described in U.S. Pat. Nos. 4,190,040 and 4,428,364.

Generally speaking, the injection button or reservoir is connected to the inflatable shell with a thin temporarily bioimplantable tube. Such structures having a "remote valve" are described, for example, in U.S. Pat. Nos. 4,217,889 and 4,190,040.

In an alternative construction of tissue expander devices, the injection reservoir is incorporated in the interior of the expandable shell. Such a tissue expander having a "self-contained" valve is described in U.S. Pat. No. 4,428,364. An advantage of this "self-contained" construction is that the entire tissue expander device is more compact, so that surgical implantation is simplified. However, in tissue expanders of this type, the surgeon usually has some difficulty in finding, for the purpose of inserting a hypodermic needle, the injection reservoir. Under these circumstances, it is difficult to be certain that only the injection reservoir, rather than the thin inflatable shell of the tissue expander, is pierced by the needle. In order to enable the surgeon to find the injection reservoir located beneath the apex of the inflatable shell, a palpation ring is provided in the prior art. The palpation ring, which is also implanted beneath the skin to surround the top portion of the injection reservoir, is then detected by the surgeon, and the hypodermic needle is inserted substantially in the center of the skin area located above the palpation ring.

A serious disadvantage of the above-summarized state-of-the-art tissue expanders having a "self-contained" valve is that the palpation ring tends to negatively affect the overlying tissue. Furthermore, even with the palpation ring, the injection reservoir is often hard to find, so that accidental puncture of the inflatable thin shell of the tissue expander is relatively common. Still further, the thin inflatable shell or bag has a tendency during implantation, and therafter, to fold over itself. Consequently, in the state-of-the-art tissue expanders having "self-contained" valves, a portion of the thin bag may actually be disposed above the injection reservoir. In such a case, of course, insertion of the hypodermic needle, even in the desired location in the center of the palpation ring, necessarily results in puncture of the inflatable shell.

In light of the foregoing, there is a definite need in tha art for an improved tissue expander device having a self-contained valve which avoids the foregoing disadvantages. The present invention provides such an improved tissue expander.

SUMMARY OF THE INVENTION

It is an object of the present invention to provide a tissue expander device having a "self-contained" injection valve or reservoir, in which the location of the injection reservoir is readily ascertained after implantation.

It is another object of the present invention to provide a tissue expander device having a "self-contained" injection valve or reservoir, in which the danger of accidental puncture of the inflatable shell is minimized.

It is still another object of the present invention to provide a tissue expander device having a "self-contained" injection valve or reservoir, in which damage to surrounding tissue due to presence of palpation rings or like devices is minimized or eliminated.

The foregoing and other objects and advantages are attained by a tissue expander having a thin inflatable shell which incorporates a reinforcing member or insert centered substantially at the apex of the shell. The reinforcing member is substantially more rigid than the inflatable shell. The reinforcing member preferably is molded to conform to the shape of the top surface of the inflated shell, and usually has spherical curvature. Preferably its thickness decreases gradually in a radially outward direction. The injection reservoir is affixed to the shell so that its center substantially coincides with the center of the reinforcing member.

In accordance with another aspect of the invention, a strong magnet or magnetizable material is incorporated in the injection reservoir. The magnet can be located by a suitable magnetic locator device, so that, after implantation, the location of the injection reservoir is readily ascertained by a surgeon.

The features of the present invention can be best understood, together with further objects and advantages, by reference to the following description, taken in connection with the accompanying drawings.

BRIEF DESCRIPTION OF THE DRAWINGS

FIG. 4 is an enlarged cross-sectional view of the first preferred embodiment, the cross-section being taken on lines 4,4 of FIG. 2;

FIG. 5 is a schematic exploded perspective view of the injection reservoir of the first preferred embodiment;

FIG. 6 is a series of schematic cross-sectional views showing the formation of a dome-shaped sealing member of the first preferred embodiment;

FIG. 7 is a schematic view, showing the process of locating, with magnetic detector means, the injection reservoir of the first preferred embodiment, and FIG. 8 is an enlarged partial cross-sectional view of a second preferred embodimnt, the view being analogous to the one taken on lines 4,4 of FIG. 2.

DESCRIPTION OF THE PREFERRED EMBODIMENTS

The following specification taken in connectin with the drawings sets forth the preferred embodiments of the present invention. The embodiments of the invention disclosed herein are the best modes contemplated by the inventors for carrying out their invention in a commercial environment, although it should be understood that various modifications can be accomplished within the scope of the present invention.

Figure 1:
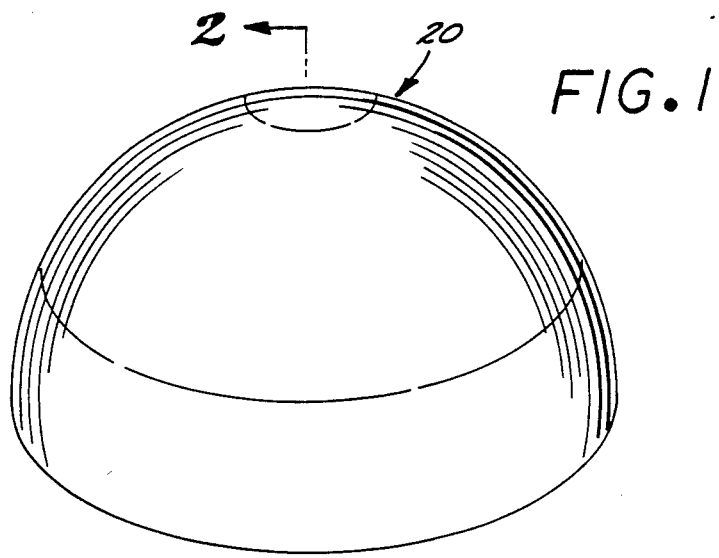
FIG. 1 is a schematic perspective view of the first preferred embodiment of the tissue expander of the present invention.
Figure 2:
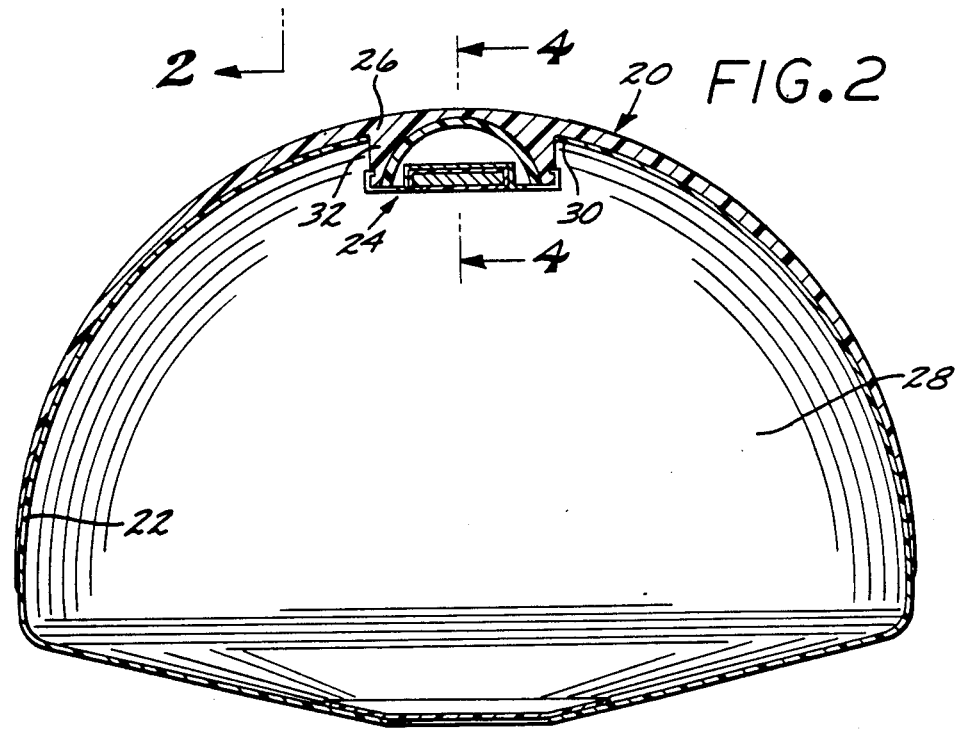
FIG. 2 is a cross-sectional view of the first preferred embodiment, the cross-section being taken on lines 2,2 of FIG. 1.

Referring now to FIGS. 1–7 of the appended drawings, and particularly to the cross-sectional views of FIGS. 2 and 4, a first preferred embodiment 20 of the tissue expander device of the present invention is disclosed. In accordance with the present invention, the tissue expander 20 includes an inflatable shell 22, an injection reservoir 24 "self-contained" in the shell 22, and a reinforcing member or insert 26. Although the drawing shows a substantially hemi-spherical tissue expander, the tissue expander of the present invention can be of any shape.

More particularly, the inflatable shell 22 is a thin expandable membrane made of a biocompatible elastic material, preferably cast medical grade silicone elastomer of a thickness of approximately 0.015". The purpose and function of the thin expandable shell 22 is to form a chamber 28 into which saline solution (or some other medically acceptable liquid) is injected from time to time to expand the chamber 28 and thereby enlarge the skin and subcutaneous layer under which the tissue expander 20 is temporarily implanted. In other words, the thin expandable shell 22 is, generally speaking, of the type normally used in state-of-the-art tissue expanders. For a general description of such tissue expanders, reference is made to U.S. Pat. No. 4,217,889, the specification of which is hereby expressly incorporated by reference. The inflatable shell 22 is configured to include an apex 30, where the injection reservoir 24 is affixed to the shell 22.

As an important novel feature of the present invention, the reinforcing member or insert 26 is affixed to the thin expandable shell 22 by vulcanization or through the use of a suitable adhesive (not shown). The reinforcing member 26 is preferably disc shaped when flattened. As is shown on the drawing Figures, the reinforcing member 26 is affixed to the shell 22 in a configuration wherein its center substantially coincides with the apex 30 of the shell 22, and also with the center of the injection button or reservoir 24.

Figure 3:
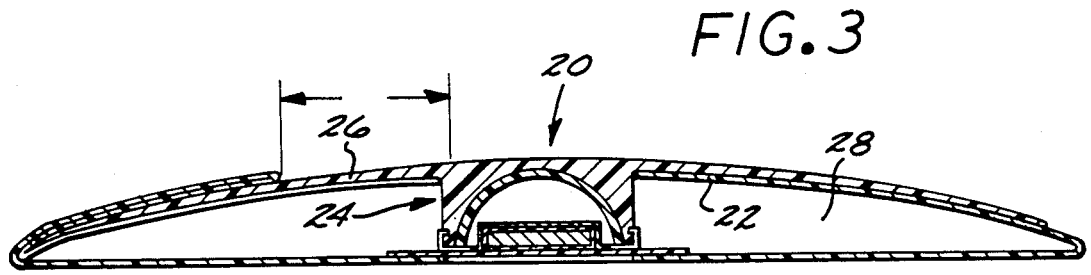
FIG. 3 is another cross-sectional view showing the maximum possible folding of a thin expandable shell over a reinforcing member of the first preferred embodiment.

The principal function of the reinforcing member or insert 26 is to substantially prevent the thin shell 22 from folding over itself and the injection reservoir 24, and thereby to substantially prevent accidental puncture of the shell 22 when a hypodermic needle (not shown) is used to pierce the injection reservoir 24. For this purpose, the reinforcing member 26 is made substantially more rigid than the inflatable shell 22. Preferably, as in the herein-described preferred embodiments, the reinforcing member 26 comprises twenty-five (25) durometer molded, medical grade silicone elastomer. The reinforcing member 26 is preferably molded to conform to the shape of the inflated shell 22, and usually has spherical curvature. The reinforcing member 26 preferably has a radially outwardly gradually decreasing thickness which changes between approximately 0.1" substantially in the center, to approximately 0.020" substantially at the edge of the reinforcing member 26. Still more preferably, the thickness of the reinforcing member 26 gradually decreases from approximately 0.070" substantially in the center, to approximately 0.020" substantially at the edge of the reinforcing member 26. FIG. 3 shows schematically how the reinforcing member 26 prevents folding of the shell 22 over itself to such an extent so as to present a danger for accidental puncture by a hypodermic needle (not shown) which is directed to the injection reservoir 24.

Referring again principally to FIGS. 2 and 4, in the herein-described first preferred embodiment 20 the reinforcing member 26 is shown attached to the thin shell 22 on the exterior of the shell 22. Moreover, the reinforcing member 26 includes an inwardly projecting cylindrical member 32, having an open bottom 34. The cylindrical member 32 is integrally molded with the reinforcing member 26. A circular opening 35 is present in the apex of the expandable shell 22 to accommodate the inwardly projecting cylindrical member 32. As is best shown on the exploded view of Figure 5, the cylindrical member 32 comprises the outer wall of the injection reservoir 24. Remaining components of the injection reservoir 24 of the first preferred embodiment 20 are mounted into the cylindrical member 32. It is noted, however, in connection with the detailed description of the injection reservoir 24, that, whereas the hereinafter-described injection reservoir 24 of the first preferred embodiment 20 is novel, several other types of injection reservoirs may be used in connection with the present invention, the important factor being only that the injection reservoir be "self-contained", that is, included in the tissue expander itself, and not merely connected thereto by a suitable conduit or tube (not shown).

The injection reservoir 24 of the first preferred embodiment 20, thus, includes a substantially hemi-spherically shaped concave wall 36 which is formed in the interior of the reinforcing member 26, and which is rimmed by the cylindrical member 32. A substantially dome-shaped sealing plate or member 38 is affixed to the concave wall 36 by adhesive or other suitable means. The dome-shaped sealing member 38 is formed by molding from medical grade silicone elastomer (or like elastic material) a hollow hemi-sphere or dome 40, and thereafter inverting it, as is shown schematically in the series of drawings of FIG. 6. The sealing member 38 is self-sealing to punctures by a hypodermic needle (not shown) because, due to the inversion, its inner wall is in compression. A more detailed description of injection reservoirs incorporating such an inverted dome type sealing member is found in the co-pending application for U.S. Letters Patent of J. C. Hancock, W. R. Dubrul, and C. J. Heyler, titled SELF-SEALING INJECTION RESERVOIR, assigned to the same assignee as the present application, Ser. No. 781,965, filed on Sept. 30, 1985.

A lower closing member 42 of the injection reservoir 24 is best shown in detail in FIGS. 4 and 5. Thus, the substantially disc-shaped metal closing member 42 has a plurality of protruding thongs 44 and a recess 46 located in its bottom. The lower closing member 42 preferably comprises stainless steel. The thongs 44 are used for attaching the lower closing member to the cylindrical outer wall 32 of the injection reservoir 24, as is best shown on FIG. 4. A strong permanent magnet 48 is located in the recess 46, and is embedded therein in plastic resin 50 or other encapsulating material, such as vapor barriers including stainless steel or glass, which is itself embedded in a silicone elastomer. The resin coating or embedding material 50 of the magnet 48 is shown on FIG. 4. The permanent magnet 50 preferably is a samarium cobalt or neodymium magnet. The purpose and function of the magnet 50 is described below. The lower closing member 42 serves as a needle guard to prevent inadvertent over-extension of a hypodermic needle (not shown). The needle guard 42 therefore prevents inadvertent puncture of the inflatable shell 22 which is disposed below the injection reservoir 24. An opening or slit 51 in the needle guard 42 allows fluid communication between the injection reservoir 24 and the chamber 28 of the tissue expander 20.

Referring now to FIG. 7, a magnet locator 52 is schematically shown. The magnet locator 52 is used in conjunction with the tissue expander of the present invention to locate the position of the injection reservoir 24 below the skin 54 and subcutaneous tissue (not shown), thereby enabling a surgeon (not shown) to inject or withdraw liquid (not shown) from the tissue expander. In this regard, it is noted that the magnet locator 52 may be constructed in accordance with several principles well known in the art. For example, the magnet locator 52 may include electronic circuitry (not shown) of the well-known type, similar to circuitry used in common metal detectors. Alternatively, the magnet locator 52 may be based on the principles of ordinary "stud finders" used in construction and home repair, wherein a tipping of a movably mounted magnet of the locator 52 indicates the presence of a magnet or magnetizable metal immediately below the locator 52. U.S. Pat. No. 3,845,384, the specification of which is expressly incorporated herein by reference, for example, describes a stud finder, the principles of operation and construction of which can be readily adapted to construct a magnet locator usable in connection with the present invention. The magnet detector 52, even if it is the mechanical type (such as the one described in U.S. Pat. No. 3,845,384) preferably includes a light source 56 and an electric circuit (not shown) which is closed to energize the light source 56 when the magnet 48 is disposed directly below the detector 52.

Inasmuch as the magnet locator 52 is capable of, or can be adapted to locate magnetizable material rather than a magnet, the needle guard 42 may be of stainless steel or other acceptable suitable magnetizable material, in which case the magnet 50 may not be necessary.

Referring now to FIG. 8, a second preferred embodiment 58 of the tissue expander is disclosed. Principal differences between the first preferred embodiment 20 and the second preferred embodiment 58 are as follows. In the second preferred embodiment 58 the reinforcing member 26 is attached to the interior, not to the exterior of the thin expandable shell 22. The reinforcing member 26 includes, substantially in its center, a recess 60 into which an outer housing member 62 of the injection reservoir 24 is mounted by vulcanization or a suitable adhesive. The reinforcing member 26 is preferably approximately 0.030" thick in the area of the recess 60.

Several advantages of the hereinabove-described self-contained tissue expander device include the lack of palpation rings, which, in the prior art, tend to cause tissue necrosis and related problems. Moreover, the permanent magnet included in the tissue expander of the present invention renders it relatively easy for the surgeon to find the injection reservoir of the temporarily implanted tissue expander. Still further, the inability of the shell 22 to fold over the injection reservoir 24 substantially prevents inadvertent puncturing of the inflatable shell 22.

Several modifications of the above-described tissue expander may become readily apparent to those skilled in the art in light of the foregoing disclosure. Particularly apparent modifications may lie in the nature and construction of the sealing plate or member which is included in the "self-contained" injection reservoir of the tissue expander. Therefore, the scope of the present invention should be interpreted solely from the following claims, as such claims are read in light of the foregoing disclosure.

What is claimed is:

1. A tissue expander device for surgical implantation beneath the skin and the subcutaneous layer, the tissue expander comprising:
   a base;
   a thin expandable cover comprising biocompatible elastic material attached to the base, the base and the cover jointly forming an expandable fluid-tight chamber, the cover having an apex;
   an injection reservoir fully enclosed in the chamber attached to the interior of the cover substantially at the apex of the cover, and being in fluid communication with the chamber, the injection reservoir comprising means for receiving injection of a liquid into the reservoir with a hypodermic needle which punctures the injection reservoir, and means for substantially leak-proof sealing of the needle puncture in the injection reservoir after the needle is withdrawn from the reservoir, and
   a reinforcing member affixed to the cover where the injection reservoir is affixed to the cover, the center of the reinforcing member being affixed to the cover substantially at the apex of the cover, the reinforcing member being larger in area than the injection reservoir, being substantially more rigid than the thin cover and comprising means for substantially preventing the thin cover from folding upon itself during implantation and thereafter, and thereby comprising means for minimizing accidental puncture of the cover by the hypodermic needle.

2. The tissue expander device of claim 1 wherein the reinforcing member comprises a sheet of biocompatible material having substantially greater thickness than the thin cover.

3. The tissue expander device of claim 2 wherein the reinforcing member comprises molded silicone rubber.

4. The tissue expander device of claim 1 wherein the cover comprises a cast shell of silicone rubber.

5. The tissue expander device of claim 1 further comprising magnetically detectable material incorporated in the injection reservoir, whereby the injection reservoir can be located from the outside by means for locating magnetic material.

6. The injection reservoir of claim 5 wherein the magnet is permanent and is selected from the group consisting of a rare earth metal cobalt magnet and neodymium magnet.

7. The tissue expander device of claim 1, wherein the injection reservoir comprises:
an outer wall;
a substantially dome-shaped sealing member affixed to the outer wall, the sealing member being disposed in a location where a hypodermic needle is normally pierced through the injection reservoir to add or withdraw liquid from the tissue expander through the injection reservoir, the sealing member being self-sealing to punctures by the hypodermic needle; and
a needle guard assembly affixed to substantially the bottom of the outer wall, the needle guard assembly comprising a metal plate and magnetically detectable material, the magnetically detectable material comprising means for enabling external magnet locator means for locating the injection reservoir when the tissue expander is implanted beneath the skin and subcutaneous tissue of a patient.

8. The injection reservoir of claim 7 wherein the magnetically detectable material is a permanent magnet.

9. The injection reservoir of claim 7 wherein the needle guard assembly is a plate including a recess, the opening of said recess faces the interior of the tissue expander, and wherein the magnetically detectable material is mounted in the recess.

10. The injection reservoir of claim 9 wherein the magnetically detectable material is mounted in the recess is embedded in plastic resin.

11. The injection reservoir of claim 10 wherein the plastic resin embedding the magnetically detectable material is further embedded in a silicone elastomer.

12. A tissue expander device for surgical implantation beneath the skin and the subcutaneous layer of the type which is expanded after implantation by periodic injection of a liquid, such as saline into the expander device, the tissue expander comprising:
a thin expandable biocompatible cast silicone elastomer envelope forming an expandable fluid-tight chamber, the chamber being configured to include an apex;
an injection reservoir fully enclosed in the chamber, affixed to the interior of the envelope substantially in the proximity of the apex, and being in fluid communication with the chamber, the injection reservoir comprising means for receiving injection of a liquid into the reservoir with a hypodermic needle which punctures the injection reservoir, and means for substantially leak-proof sealing of the needle puncture in the injection reservoir after the needle is withdrawn from the reservoir, and
a reinforcing member configured to substantially conform to the shape of the envelope when said envelope is inflated, substantially centered at the apex of the chamber, the reinforcing member being larger in area than the injection reservoir, being substantially more rigid than the thin envelope, the thickness of the reinforcing member decreasing substantially gradually from approximately 0.1" at its center to approximately 0.020" substantially at the edge of the reinforcing member, the reinforcing member comprising means for substantially preventing the thin envelope from folding upon itself during implantation or thereafter, and thereby comprising means for minimizing accidental puncture of the envelope by the hypodermic needle.

13. The tissue expander of claim 10 wherein the thin envelope is approximately 0.015" thick.

14. The tissue expander of claim 10 wherein the reinforcing member comprises silicone elastomer.

15. The tissue expander of claim 10 wherein the injection reservoir includes a magnet, whereby location of the injection reservoir can be determined by means for locating the magnet.

16. The tissue expander of claim 15 wherein the magnet in the injection reservoir is embedded in vapor barrier material.

17. In a tissue expander used for surgical implantation beneath the skin and the subcutaneous layer of the type which is expanded after implantation by periodic injection of liquid into the expander device, the tissue expander having an expandable biocompatible envelope forming an expandable fluid-tight chamber configured to include an apex and an injection reservoir fully enclosed in the chamber affixed in the interior of the envelope substantially in the proximity of the apex, and being in fluid communication with the chamber, the injection reservoir comprising means for receiving injection of a liquid into the reservoir with a hypodermic needle which punctures the injection reservoir, and means for substantially leak-proof sealing of the needle puncture in the injection reservoir after the needle is withdrawn from the reservoir, the improvement comprising:
a reinforcing member affixed to the envelope where the injection reservoir is affixed to the envelope, the reinforcing member being larger in area than the injection reservoir, being centered substantially in the center of the apex, being substantially more rigid than the envelope, being configured to substantially conform to the shape of the envelope when the envelope is inflated and having a thickness which decreases gradually outwardly from the center of the reinforcing member to its edge, the reinforcing member comprising means for substantially preventing the envelope from folding upon itself during implantation or thereafter, and thereby comprising means for minimizing accidental puncture of the envelope by the hypodermic needle.

18. The improvement of claim 17 wherein the thickness of the reinforcing member decreases from approximately 0.1" to approximately 0.020" substantially at its edge.

19. The improvement of claim 18 wherein the thickness of the reinforcing member decreases from approximately 0.070" to approximately 0.030" substantially at its edge.

20. The improvement of claim 17 wherein the reinforcing member is affixed to the interior of the envelope.

21. The improvement of claim 17 wherein the reinforcing member is affixed to the exterior of the envelope.

22. The improvement of claim 17 further comprising a magnet incorporated in the injection reservoir whereby location of the injection reservoir can be ascertained by external means for locating the magnet.

23. In a tissue expander used for surgical implantation beneath the skin and the subcutaneous layer of the type which is expanded after implantation by periodic injection of a liquid into the expander device, the tissue expander having an expandable biocompatible envelope forming an expandable fluid-tight chamber configured to include an apex and an injection reservoir fully enclosed in the chamber attached to the interior of the envelope substantially in the proximity of the apex, and being in fluid communication with the chamber, the injection reservoir comprising means for receiving injection of a liquid into the reservoir with a hypodermic needle which punctures the injection reservoir, and means for substantially leak-proof sealing of the needle puncture in the injection reservoir after the needle is withdrawn from the reservoir, the improvement comprising:

magnetically detectable material incorporated in the injection reservoir, whereby location of the injection reservoir can be ascertained by external means for locating the magnetically detectable means; and a reinforcing member affixed to the envelope where the injection reservoir is affixed to the envelope, the reinforcing member being larger in area than the injection reservoir, being centered substantially in the apex of the envelope, configured to substantially conform to the shape of the envelope when the envelope is inflated, being substantially more rigid than the envelope, having a thickness which decreases gradually outward substantially from the center of the reinforcing member toward its edge, the reinforcing member comprising means for substantially preventing the envelope from folding upon itself during implantation or thereafter, and thereby comprising means for minimizing accidental puncture of the envelope by the hypodermic needle.

* * * * *